(12) United States Patent
Delano et al.

(10) Patent No.: US 9,295,715 B2
(45) Date of Patent: Mar. 29, 2016

(54) MINIMIZING INTESTINAL DYSFUNCTION

(75) Inventors: Frank A. Delano, San Diego, CA (US); Geert W. Schmid-Schonbein, Del Mar, CA (US); Darin Saltzman, Glendale, CA (US)

(73) Assignee: The Regents of the University of California, Oakland, CA (US)

( * ) Notice: Subject to any disclaimer, the term of this patent is extended or adjusted under 35 U.S.C. 154(b) by 91 days.

(21) Appl. No.: 13/876,943

(22) PCT Filed: Oct. 3, 2011

(86) PCT No.: PCT/US2011/054640
§ 371 (c)(1),
(2), (4) Date: Sep. 17, 2013

(87) PCT Pub. No.: WO2012/045083
PCT Pub. Date: Apr. 5, 2012

(65) Prior Publication Data
US 2014/0018293 A1   Jan. 16, 2014

Related U.S. Application Data

(60) Provisional application No. 61/389,209, filed on Oct. 2, 2010.

(51) Int. Cl.
| | | |
|---|---|---|
| A61K 38/00 | (2006.01) |
| A61K 31/00 | (2006.01) |
| A61K 38/38 | (2006.01) |
| A61K 31/415 | (2006.01) |
| A61K 31/496 | (2006.01) |
| A61K 31/4965 | (2006.01) |
| A61K 45/06 | (2006.01) |
| A61K 31/195 | (2006.01) |
| A61K 31/497 | (2006.01) |

(52) U.S. Cl.
CPC ............... *A61K 38/38* (2013.01); *A61K 31/195* (2013.01); *A61K 31/415* (2013.01); *A61K 31/496* (2013.01); *A61K 31/497* (2013.01); *A61K 31/4965* (2013.01); *A61K 45/06* (2013.01)

(58) Field of Classification Search
CPC ...................................................... A61K 38/00
See application file for complete search history.

(56) References Cited

U.S. PATENT DOCUMENTS

| | | |
|---|---|---|
| 5,171,321 A | 12/1992 | Davis |
| 5,743,272 A | 4/1998 | Kocher, Jr. |
| 5,993,427 A | 11/1999 | Rolland et al. |
| 6,344,189 B1 | 2/2002 | Bunn et al. |
| 6,455,027 B1 | 9/2002 | Barsky et al. |
| 6,534,283 B1 | 3/2003 | Schmid-Schoenbein et al. |
| 6,610,274 B1 | 8/2003 | Gardner |
| 6,664,287 B2 | 12/2003 | Avery et al. |
| 7,084,141 B2 | 8/2006 | Gaeta et al. |
| 7,368,529 B2 | 5/2008 | Upadhyay et al. |
| 7,713,737 B2 | 5/2010 | Mrsny |
| 7,763,253 B2 | 7/2010 | Hedlund |
| 7,906,140 B2 | 3/2011 | Bromley et al. |
| 8,541,371 B2 | 9/2013 | Schmid-Schonbein et al. |
| 8,841,258 B2 | 9/2014 | DeLano et al. |
| 2002/0037265 A1 | 3/2002 | Hung et al. |
| 2002/0114815 A1 | 8/2002 | Barsky et al. |
| 2002/0117169 A1 | 8/2002 | Kurz et al. |
| 2003/0060488 A1 | 3/2003 | Sugiyama et al. |
| 2004/0014024 A1 | 1/2004 | Yayon et al. |
| 2005/0037022 A1 | 2/2005 | Rosen et al. |
| 2006/0211752 A1 | 9/2006 | Kohn et al. |
| 2006/0216757 A1 | 9/2006 | Brines et al. |
| 2007/0142337 A1 | 6/2007 | Schmid-Schonbein et al. |
| 2007/0148214 A1 | 6/2007 | Cullen et al. |
| 2007/0292407 A1 | 12/2007 | Ivanov |
| 2007/0294107 A1 | 12/2007 | Schmid-Schonbein et al. |
| 2010/0179091 A1 | 7/2010 | Schmid-Schonbein et al. |
| 2010/0303799 A1 * | 12/2010 | Schmid-Schonbein et al. ........... 424/94.64 |
| 2011/0039781 A1 | 2/2011 | Schmid-Schonbein |
| 2013/0158394 A1 | 6/2013 | Hon et al. |
| 2013/0231309 A1 | 9/2013 | Schmid-Schonbein et al. |

FOREIGN PATENT DOCUMENTS

| | | |
|---|---|---|
| EP | 1185309 | 3/2002 |
| GB | 2400037 | 10/2004 |
| JP | H7-31829 | 6/1995 |
| JP | 2004-523307 | 8/2004 |
| WO | 2008/103767 | 8/2008 |
| WO | 2009/045543 | 4/2009 |
| WO | 2009/132149 | 10/2009 |
| WO | 2011/038417 | 3/2011 |
| WO | 2011/088392 | 7/2011 |

OTHER PUBLICATIONS

Yasuda et al. (J Gastroenterol 2007; 42:681-689).*
O'Brien et al. (Inflammation V 24 N5, 2000, pp. 411-429).*
Eilliott (Gastroenterology Apr. 1955, pp. 563-592).*
Steven D. Freedman (Merck Oct. 2012, acute pancreatitis).*
EP11830068 Supplementary European Search Report mailed on Mar. 12, 2014.
JP2012-549138 Office Action mailed Sep. 12, 2014.
PCT/US2011/021395 International Search Report mailed Aug. 30, 2011.
Aoki, et al. "Blood-brain barrier disruption and matrix metalloproteinase-9 expression during reperfusion injury: mechanical versus embolic focal ischemia in spontaneously hypertensive rats." Stroke 2002, 33:2711-2717.

(Continued)

*Primary Examiner* — Karlheinz R Skowronek
*Assistant Examiner* — Li Lee
(74) *Attorney, Agent, or Firm* — Wagenknecht IP Law Group PC

(57) ABSTRACT

Techniques are disclosed for treating or reducing symptoms associated with abdominal dysfunction or ileus following surgery or other abdominal episode by treating the area with a combination of one or more protease, antibacterial compound, and inflammatory lipid mediator.

20 Claims, 2 Drawing Sheets

(56) References Cited

OTHER PUBLICATIONS

Arndt et al. "Leukocyte-endothelial cell adhesion in spontaneously hypertensive and normotensive rats." Hypertension 1993, 21: 667-673.
Asanuma et al. "Uniaxial strain upregulates matrix-degrading enzymes produced by human vascular smooth muscle cells." Am J Physiol Heart Circ Physiol 2003, 284: H1778-1784.
Bergman et al. "Single-dose Chemoprophylaxis in Elective Colorectal Surgery." Ann. Surg, 1987, 205(1): 77-81.
Biggs et al. "Tranexamic acid and upper gastrointestinal haemorrhage—a double-blind trial." Gut, 1976, 17: 729-734.
Bursztyn et al. "Insulin resistance in spontaneously hypertensive rats but not in deoxycorticosterone-salt or renal vascular Hypertension." Journal of Hypertension 1992, 10: 137-142.
Cakir et al. "Direct action by doxycycline against canine osteosarcoma cell proliferation and collagenase (MMP-1) activity in vitro." In Vivo 1999,13: 327-331.
Camp et al. "Mechanism of matrix accumulation and glomerulosclerosis in spontaneously hypertensive rats." J Hypertens 2003, 21: 1719-1727.
D'Agostino et al. ""Doxycycline reduces mortality to lethal endotoxemia by reducing nitric oxide synthesis via an interleukin-10-independent mechanism. J Infect Dis., 1998, 177(2):489-92.
Deitch et al. "Serine proteases are involved in the pathogenesis of trauma-hemorrhagic shock-induced gut and lung injury." Shock 2003, 19:452-456.
De Lano et al., "A possible role of matrix metalloproteinases in cellular injury of the spontaneously hypertensive rat", FASEB J 2003, 17: A346.330.
De Lano et al. "Control of oxidative stress in microcirculation of spontaneously hypertensive rats." Am J Physiol Heart Circ Physiol 2005, 288: H805-812.
De Lano et al. "Microvascular Display of Xanthine Oxidase and NADPH Oxidase in the Spontaneously Hypertensive Rat." Microcirculation 2006, 13(7):551-66.
De Lano et al. "Enhancement of glucocorticoid and Mineralocorticoid Receptor Density in the Microcirculation of the Spontaneously Hypertensive Rat." Microcirculation 2004, 11: 69-78.
De Lano et al. "Visualization of enhanced matrix metalloproteinase activity in the spontaneously hypertensive rat by a fluorogenic substrate." FASEB J 2005, 19: A1263.
De Lano and Schmid-Schonbein. "Proteinase activity and receptor cleavage: mechanism for insulin resistance in the spontaneiously hypertensive rat," Hypertension 2008, 52:415-23.
Doucet, et al. "Inhibition of enteral enzymes by enteroclysis with nafamostat mesilate reduces neutrophil activation and transfusion requirements after hemorrhagic shock." J Trauma 2004, 56:501-511.
Duivenvoorden et al. "Use of tetracycline as an inhibitor of matrix metalloproteinase activity secreted by human bone-metastasizing cancer cells." Invasion Metastasis 1997, 17: 312-322.
Ergul et al. "Stress upregulates arterial matrix metalloproteinase expression and activity via endothelin: A receptor activation." Am J Physiol Heart Circ Physiol 2003, 285: H2225-2232.
Fitzal et al. "Pancreatic enzymes sustain systemic inflammation after an initial endotoxin challenge." Surgery 2003, 134:1-11.
Fitzal et al. "Improvement in early symptoms of shock by delayed intestinal protease inhibition", Arch Surg. 2004; 139:1008-1016.
Frears et al. "Inactivation of tissue inhibitor of metalloproteinase-1 by peroxynitrite." FEBS Lett 1996, 381: 21-24.
Galis et al. "Matrix metalloproteinases in vascular remodeling and atherogenesis: the good, the bad, and the ugly." Circ Res 2002, 90: 251-262.
Goldberg et al. "High susceptibility to bacterial infection, but no liver dysfunction, in mice compromised for hepatocyte NF-kappaβ activation." Nature Medicine, 2000, 6(5): 573-577.
Griffin et al. "Reduction of myocardial infarct size by doxycycline: a role for plasmin inhibition." Mol Cell Biochem 2005, 270: 1-11.
Grote et al. "Mechanical stretch enhances mRNA expression and proenzyme release of matrix metalloproteinase-2 (MMP-2) via NAD(P)H oxidase-derived reactive oxygen species." Circ Res 2003, 92: e80-86.
Guerciolini, R. "Mode of Action of Orlistat." J International Assoc for the Study of Obesity, (Abstract), 1997, 21 Suppl 3:S12-23.
Hanazaki et al. "The protective effect of urinastatin in patients with ileus." Acta Medica et Biologica, 1994, 42(3): 129-132.
Hanemaaijer et al. "Matrix metalloproteinase-8 is expressed in rheumatoid synovial fibroblasts and endothelial cells. Regulation by tumor necrosis factor-alpha and doxycycline." J Biol Chem, 1997, 272: 31504-31509.
Hanemaaijer et al. "Inhibition of MMP Synthesis by Doxycycline and Chemically Modified Tetracyclines (CMTs) in Human Endothelial Cells." Adv Dent Res Nov. 1998, 12:114-118.
Hashimoto et al. "Amyloidosis of the small intestine secondary to rheumatoid arthritis and juvenile rheumatoid arthritis: report of two cases." Rheumatism, Feb. 1995, 35(1): 100-106.
Hulman et al. "Insulin resistance in the conscious spontaneously hypertensive rat: euglycemic hyperinsulinemic clamp study." Metabolism: Clinical and Experimental 1993, 42: 14-18.
Ishimaru et al. "Pancreatic Proteases and Inflammatory Mediators in Peritoneal Fluid During Splanchnic Arterial Occlusion and Reperfusion." Shock 2004, 22(5):467-471.
Kim et al. "Doxycycline inhibits TGF-beta1-induced MMP-9 via Smad and MAPK pathways in human corneal epithelial cells." Invest Ophthalmol Vis Sci 2005, 46: 840-848.
Kobayashi et al. "Oxidative stress promotes endothelial cell apoptosis and loss of microvessels in the spontaneously hypertensive rats." Arterioscler Thromb Vasc Biol 2005, 25: 2114-2121.
Kolev et al., "Matrix metalloproteinase-9 expression in post-hypoxic human brain capillary endothelial cells: $H_2O_2$ as a trigger and NF-kappaB as a signal transducer." Thromb Haemost 2003, 90: 528-537.
Krakauer and Buckley. "Doxycycline is anto-inflammatory and inhibits staphylococcal exotoxin-induced cytokines and chemokines." Antimicrob Agents Chemother, Nov. 2003, 47(11): 3630-3.
Krier et al. "Management of Severe Clostridium difficile-Associated Diarrhea." Digestive Diseases and Sciences, Feb. 19, 2009, 54(6):1199-1202, Kluwer Academic Publishers-Plenum Publishers, NE.
Kuzuya et al. "Role of matrix metalloproteinases in vascular remodeling." J Atheroscler Thromb 2003, 10: 275-282.
Lamparter et al. "Doxycycline and tissue repair in rats." J Lab Clin Med 2002, 139: 295-302.
Le, Jennifer. "Drug Absorption". Merck Manual "Pharmacokinetics in Children" 2010-2013 [retrieved from internet] http://www.merckmanuals.com/professional/print/clinical_pharmacology/pharmacokinetics/drug_absorption.html.
Lee et al. Doxycycline reduces airway inflammation and hyper-responsiveness in a murine model of toluene diisocyanate-induced asthma. J Allergy Clin Immunol., May 2004, 113(5): 902-9.
Lehoux et al. "Pressure-induced matrix metalloproteinase-9 contributes to early hypertensive remodeling." Circulation 2004, 109: 1041-1047.
Lenda et al. "Reactive oxygen species may contribute to reduced endothelium-dependent dilation in rats fed high salt." Am J Physiol Heart Circ Physiol 2000, 279: H7-H14.
Li et al. "MMP/TIMP expression in spontaneously hypertensive heart failure rats: the effect of ACE- and MMP-inhibition." Cardiovasc Res 2000, 46: 298-306.
Liesenfeld et al. Poster #89, Wound Healing Society, 2006, [retrieved from internet on Mar. 17, 2014] http://content.stockpr.com/qmdt/media/d166915d079a967f12e6c9f114cb0ab.1.pdf.
Lim et al. "Life and death cell labeling in the microcirculation of the spontaneously hypertensive rat." J Vasc Res 2001, 38: 228-236.
Lip et al., "Soluble adhesion molecule P-selectin and endothelial dysfunction in essential Hypertension: implications for atherogenesis? A preliminary report." Journal of Hypertension 1995,13: 1674-1678.

(56) References Cited

OTHER PUBLICATIONS

Madan et al., "Use of Ciprofloxacin in the Treatment of Hospitalized Patients with Intra-abdominal Infections", Clinical Therapeutics 2004, 26(10):1564-77.
Masahiro et al. "A case of severe intestinal tuberculosis, treated with ciprofloxacin, kanamycin and prednisolone." Tuberculosis, Apr. 2006, 81(4): 345-349.
Morisco et al. "Insulin-stimulated cardiac glucose uptake is impaired in spontaneously hypertensive rats: role of early steps of insulin signaling." Journal of Hypertension 2000, 18: 465-473.
Muhs et al. "Inhibition of matrix metalloproteinases reduces local and distant organ injury following experimental acute pancreatitis", J Surg Res. 2003; 109:110-17.
Mujumdar et al. "Activation of matrix metalloproteinase dilates and decreases cardiac tensile strength." Int J Cardiol 2001, 79: 277-286.
Newaz et al. "Modulation of nitric oxide synthase activity in brain, liver, and blood vessels of spontaneously hypertensive rats by ascorbic acid: protection from free radical injury." Clin Exp Hypertens 2005, 27: 497-508.
Newman et al., "Circular dichroism spectra of tetracycline complexes with Mg+2 and Ca+2." J Pharm Sci 1976, 65: 1728-1732.
Penn et al. "Pancreatic enzymes generate cytotoxic mediators in the intestine", Shock 2007, 27(3):296-304.
Penn et al., "The Intenstine as Source of Cytotoxic Mediators in Shock: Free Fatty Acids and Degradation of Lipid-Binding Proteins," Am J Physiol Heart Circ Physiol 2008, 294:H1779-92.
Peterson et al. "Matrix metalloproteinase inhibition attenuates left ventricular remodeling and dysfunction in a rat model of progressive heart failure." Circulation 2001, 103: 2303-2309.
Rajagopalan et al. "Reactive oxygen species produced by macrophage-derived foam cells regulate the activity of vascular matrix metalloproteinases in vitro. Implications for atherosclerotic plaque stability." J Clin Invest 1996, 98: 2572-2579.
Rieder et al. "Wound Healing and Fibrosis in Intestinal Disease." Gut, 2007, 56:130-139.
Ritchie. "Protease Inhibitors." Labome Material Methods, 2013, 3(169): 1-7.
Rosario et al. "Pancreatic trypsin increases matrix metalloproteinase-9 accumulation and activation during acute intestinal ischemia-reperfusion in the rat", Am J Pathol. 2004; 164:1707-16.
Rosenberg et al. "Proteolytic cascade enzymes increase in focal cerebral ischemia in rat." J Cereb Blood Flow Metab 1996, 16: 360-366.
Ryan et al., "Tetracyclines inhibit protein glycation in experimental Diabetes." Adv Dent Res 1998,12: 152-158.
Saha et al. "Efficacy of Metronidazole Lavage in Treatment of Intraperinoneal Sepsis," Digestive Disease and Science 1996, 41(7):1313-18.
Schmid-Schonbein et al. "Leukocyte counts and activation in spontaneously hypertensive and normotensive rats." Hypertension 1991, 17: 323-330.
Schmid-Schonbein, G.W . . . 2008 Landis Award lecture—Inflammation and the Autodigestion Hypothesis. Microcirculation, 2009; 16:289-306.
Schmid-Schonbein and Hugli. "A New Hypothesis for Microvascular Inflammation in Shock and Multiorgan Failure: Self-Digestion by Pancreatic Enzymes", Microcirculation. 2005; 12:71-82.
Seccia et al. "Extracellular matrix gene expression in the left ventricular tissue of spontaneously hypertensive rats." Blood Press 1999, 8: 57-64.
Sechi et al. "Abnormalities of insulin receptors in spontaneously hypertensive rats." Hypertension 1996, 27: 955-961.
Shen et al. "Circulating leukocyte counts, activation, and degranulation in Dahl hypertensive rats." Circ Res 1995, 76: 276-283.
Shen et al. "Properties of circulating leukocytes in spontaneously hypertensive rats." Biochem Cell Biol 1995, 73: 491-500.
Shi et al. "Pancreatic enzymes in the gut contributing to lung injury after trauma/hemorrhagic shock", Chin J Traumatol. 2004; 7:36-41. [abstract].
Sironi et al. "Endogenous proteolytic activity in a rat model of spontaneous cerebral stroke." Brain Res 2003, 974: 184-192.
Sorsa et al. "Doxycycline in the protection of serum alpha-1-antitrypsin from human neutrophil collagenase and gelatinase." Antimicrob Agents Chemother 1993, 37: 592-594.
Spiers et al. "Alterations in vascular matrix metalloproteinase due to ageing and chronic Hypertension: effects of endothelin receptor blockade." J Hypertens 2005, 23: 1717-1724.
Spinale, F. G. "Matrix metalloproteinases: regulation and dysregulation in the failing heart." Circ Res 2002, 90: 520-530.
Suematsu et al. "The inflammatory aspect of the microcirculation in Hypertension: oxidative stress, leukocytes/endothelial interaction, apoptosis." Microcirculation 2002, 9: 259-276.
Suematsu et al. "Impairment of selectin-mediated leukocyte adhesion to venular endothelium in spontaneously hypertensive rats." J Clin Invest 1995, 96: 2009-2016.
Sumii et al. "Involvement of matrix metalloproteinase in thrombolysis-associated hemorrhagic transformation after embolic focal ischemia in rats." Stroke 2002, 33: 831-836.
Suzuki et al. "Impaired leukocyte-endothelial cell interaction in spontaneously hypertensive rats." Hypertension 1994, 24: 719-727.
Suzuki et al. "Modification of leukocyte adhesion in spontaneously hypertensive rats by adrenal corticosteroids." J Leukoc Biol 1995, 57: 20-26.
Takase et al. "The inflammatory reaction during venous Hypertension in the rat." Microcirculation 2000, 7: 41-52.
Touyz, R. M. "Reactive oxygen species, vascular oxidative stress, and redox signaling in Hypertension: what is the clinical significance?" Hypertension 2004, 44: 248-252.
Uitto et al. "Doxycycline and chemically modified tetracyclines inhibit gelatinase A (MMP-2) gene expression in human skin keratinocytes." Ann NY Acad Sci 1994, 732: 140-151.
Weiming et al. "Treatment of Early Postoperative Small Intestinal Obstruction." (English Abstract only) Nanjing General Hospital of Nanjing Command, PLA, Clinical School of Nanjing University, 2003, 4:219-222, Nanjing, China.
Wellen and Hotamisligil. "Obesity-induced inflammatory changes in adipose tissue." J Clin Invest., Dec. 2003, 112(12): 1785-8.
Wiseman et al. The Effect of Tranexamic Acid in Firbin Sealant on Adhesion Formation in the Rat. J Biomed Mater Res B Appl Biomater, Feb. 15, 2004, 68(2): 222-230, Synedchion, Inc. Dallas, TX US.
Witek-Janusek and Raymeyer. "Sepsis in the Young Rat: Maternal Milk Protects During Cecal Ligation and Puncture Sepsis but not During Endotoxemia," Circ Shock 1991, 33(4):200-6.
Woods et al. "Oncotic pressure, albumin and ileus: the effect of albumin replacement on postoperative ileus." The American Surgeon, Nov. 1993, 59(11): 758-763.
Yamada et al. "Elastase-like enzyme in the aorta of spontaneously hypertensive rats." Virchows Arch B Cell Pathol Incl Mol Pathol 1983, 44: 241-245.
Yasmin et al. "Matrix metalloproteinase-9 (MMP-9), MMP-2, and serum elastase activity are associated with systolic Hypertension and arterial stiffness." Artenbscler Thromb Vasc Biol 2005, 25: 372.
Zweifach et al. "Micropressure-flow relationship in a skeletal muscle of spontaneously hypertensive rats." Hypertension 1981, 3: 601-614.
PCT/US2008/011529 International Preliminary Report on Patentability (IPRP) mailed Apr. 7, 2010.
PCT/US2008/054474 International Search Report and Written Opinion mailed Jun. 27, 2008.
CN201180057633 Office Action mailed Dec. 17, 2013.
CN201180006245 Office Action mailed Apr. 1, 2014.
EP11733481.3 Extended European Search Report mailed Jan. 28, 2015.

* cited by examiner

MINIMIZING INTESTINAL DYSFUNCTION

This application is a 35 U.S.C. §371 National Stage of International Application No. PCT/US2011/054640, filed Oct. 3, 2011, claiming priority to and the benefit under 35 U.S.C. §119(e) of U.S. Provisional Patent Application Ser. No. 61/389,209, filed Oct. 2, 2010, the content of each of which is hereby incorporated by reference in their entirety.

BACKGROUND OF THE SUBJECT DISCLOSURE

1. Field of the Subject Disclosure

The present subject disclosure relates to intestinal dysfunction. In particular, the present subject disclosure relates to methods to minimize intestinal dysfunction.

2. Background of the Subject Disclosure

Ileus is a common side effect for patients undergoing many types of abdominal, or sometimes other types, of surgery. It can results in many days of intestinal dysfunction, which reflects itself in discomfort and pain for the patient.

Conventional treatments typically include: bowel rest, nasogastric decompression, and aggressive rehydration; placement of a film barrier (Seprafilm, Interceed, Hylagel R, Intergel, etc.), or a chemically modified natural sugar applied absorbable wrapping around organs; and application of a sprayable (SprayGel, Intergel Adhesion Prevention Solution) adhesion barrier.

These interventions are largely designed to prevent organ adhesion. As such, they also may serve to maintain intestinal motility but were not directly designed for this purpose.

Thus, there is a need for new methods for treatment of intestinal dysfunction which do not suffer from the same disadvantages of conventional methods or drugs. The methods should be simple to administer, effective and capable of aiding individuals in diminishing or preventing harmful effects of intestinal dysfunction without suffering from the same side effects.

SUMMARY OF THE SUBJECT DISCLOSURE

The present subject disclosure provides techniques to reduce intestinal dysfunction including a lack of intestinal food transport by lack of peristalsis, after incidences of intestinal ischemia, intestinal resections and other surgical conditions associated with intestinal injury.

Abdominal surgery is associated with a significant risk for intestinal dysfunction, e.g., intestinal peristalsis, bowel movement, bowel obstruction, and cause of pain. Female abdominal surgery, spine surgery, chemotherapy and radiation treatment can also lead to ileus.

The methods of the subject disclosure can be applied to large and small incisions as well as any surgery or conditions that are associated with infections (appendicitis, etc.) and acute/chronic injury leading to the intestine. Ileus can occur in many surgical scenarios, some of which become symptomatic.

The treatment may be prophylactically administered into the abdominal cavity at the time of any surgical procedure or radiation procedures to prevent ileus. The treatment may be administered into the peritoneum and/or into the lumen of the intestine. The treatment serves to prevent scar tissue formation (fibrous webs and bands) and serves to preserve intestinal motility.

The methods according to the present subject disclosure are expected to work in situations in which an elevated mucosal permeability and inflammation are generated in the abdominal cavity (e.g., inflammatory lipids, digestive enzymes and other degrading enzymes like plasma proteases, MMPs, etc.), in appendicitis, Crohn's disease and other inflammatory bowel diseases, intestinal or abdominal infections, in intestinal resections associated dysfunction of the intestinal permeability and motility.

DETAILED DESCRIPTION OF THE SUBJECT DISCLOSURE

Figure 1:
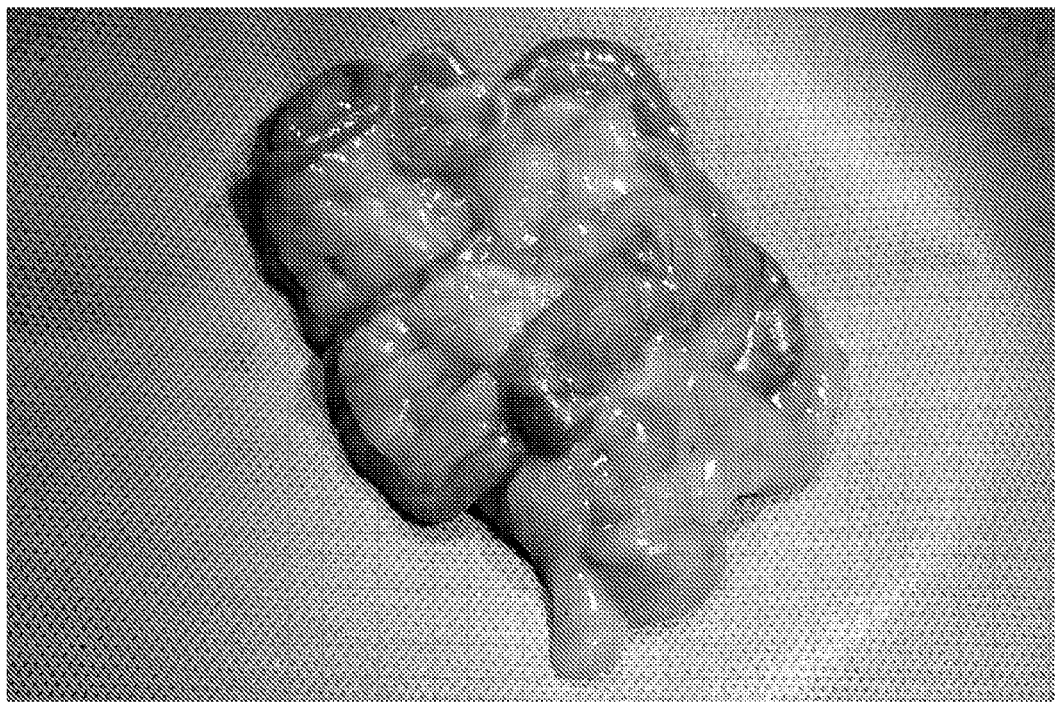
FIG. 1 shows an example view of an intestine not treated for adhesion (control group).

Ileus formation after intestinal resections or abdominal surgery is a widespread problem in surgery, radiation treatment and other therapies. The present treatment serves to minimize post treatment complications, reduce mortality, post-treatment recovery and reduce hospital stays and drug treatment.

A basic premise behind the present subject disclosure is to prevent intestinal dysfunction after general, or specifically, abdominal, surgery which manifests in the form of lack of or deficient peristaltic transport along the intestine, reduced food consumption and indigestion.

The approach is to flush all parts of the abdominal cavity during surgery, radiation treatment, and other situations that may lead to acute ileus with a solution that minimizes or prevents enzymatic degradation on the intestine and tissue damage in the wall of the intestine. The digestive enzymes in the lumen of the intestine are blocked by direct administration of digestive enzyme inhibitors (e.g., proteases) into the lumen of the intestine. If indicated by the presence of a permeable intestine or by obvious signatures of intestinal damage (e.g., appendicitis) during ileus, the treatment includes also blockade of digestive enzymes and inflammatory markers in the peritoneum together with enteral treatment.

Possible agents to be used in the methods according to the present subject disclosure include, but are not limited to, individually or in combination (depending on circumstances):

1. Enzyme (serine protease, any plasma protease, MMP, amylase and lipase) inhibitor, e.g. Cyclokapron (10 to 50 mg/100 ml);
2. Antibacterial treatment against gram-positive and gram-negative bacteria (with antibiotic treatment, e.g. ciprofloxacin, metronidazole, imipenem and cilastatin, ticarcillin and clavulanate, cefuroxime, doxycycline);
3. Inflammatory lipid mediator (e.g. free fatty acids) binding protein: Albumin (10 to 50 mg/100 ml) and equivalent.

The amount and concentrations to be administered are adjusted according to surgical site (as would be appreciated by one having ordinary skill in the art after consideration of the present disclosure), the peritoneal space to achieve complete blockade of digestive enzyme activity, binding of unbound free fatty acids, and bacterial cultures that can initiate cell damage to cell layers that coat organ surfaces (e.g., epithelial cells).

The present subject disclosure has been demonstrated in a rat model of intestinal resection and in a rat model of peritonitis (by administration of cecal material into the abdominal cavity) that blockade of the digestive enzymes in the lumen of the intestine and in the peritoneum leads to an increase of food consumption, transport along the intestine and fecal material formation without complications usually associated with ileus formation. This was achieved by treatment with a protease inhibitor in the lumen of the intestine and with a combination of protease inhibitor, antibiotic agents and free fatty acid scavenger.

The below four tables summarize the measurements of
1. Body Weight—initial weight (gm) [Table 1]
2. Food consumption (gm) [Table 2]
3. Water consumption (ml) [Table 3]
4. Fecal output (gm) [Table 4]

in the experimental rats that were subjected to intestinal resection (~3 cm right above the cecum) and either untreated or treated with luminal protease inhibitor (cyclokapron, 25 mg/ml in GoLYTELY, 18 ml over the length of the intestine) and also peritoneal treatment with a combination of protease inhibitor (cyclokapron), antibiotic (ciproflozazin) and albumin. These results show a significant protection of the intestine by a method of treatment according to the present subject disclosure: it attenuates postoperative intestinal complications (ileus) in addition to other kinds of intestinal complications (including adhesions). Normal functions (weight gain, food and water consumption, and fecal output) are resumed significantly faster with use of the present treatment versus no treatment.

TABLE 1

BODY WEIGHT CHANGE FROM INITIAL WEIGHT

| | | Post Op Day 1 | Post Op Day 2 | Post Op Day 3 | Post Op Day 4 | Post Op Day 5 | Post Op Day 6 | Post Op Day 7 |
|---|---|---|---|---|---|---|---|---|
| Weight Change (grams) | Without Treatment | −13.6 | −21.3 | −25.3 | −22.1 | −18.6 | −18.2 | −16.4 |
| | | 11.1 | 16.1 | 16.8 | 16.2 | 14.8 | 16.1 | 18.7 |
| | With Treatment | 2.8 | 1.7 | 2.1 | 2.4 | 4.5 | 7.4 | 11.6 |
| | | 7.6 | 9.6 | 10.1 | 10.2 | 9.7 | 9.9 | 10.8 |
| | ttest | 0.0036 | 0.0035 | 0.0013 | 0.0025 | 0.0022 | 0.0017 | 0.0024 |

Values are listed as mean ± SD
n = 9 without treatment
n = 7 with treatment

TABLE 2

FOOD CONSUMPTION

| | | Post Op Day 1 | Post Op Day 2 | Post Op Day 3 | Post Op Day 4 | Post Op Day 5 | Post Op Day 6 | Post Op Day 7 |
|---|---|---|---|---|---|---|---|---|
| Food Consump. (ml) | Without Treatment | 1.1 | 3.1 | 6.8 | 9.3 | 12.0 | 14.8 | 14.8 |
| | | 1.6 | 1.7 | 3.7 | 4.9 | 6.0 | 7.3 | 5.0 |
| | With Treatment | 8.7 | 9.0 | 12.0 | 18.6 | 22.5 | 24.4 | 29.7 |
| | | 4.2 | 4.2 | 5.4 | 6.0 | 5.5 | 3.6 | 5.8 |
| | ttest | 0.0024 | 0.0084 | 0.0517 | 0.0066 | 0.0029 | 0.0049 | 0.0002 |

Values are listed as mean ± SD
n = 9 without treatment
n = 7 with treatment

TABLE 3

WATER CONSUMPTION

| | | Post Op Day 1 | Post Op Day 2 | Post Op Day 3 | Post Op Day 4 | Post Op Day 5 | Post Op Day 6 | Post Op Day 7 |
|---|---|---|---|---|---|---|---|---|
| Water Consump. (ml) | Without Treatment | 3.4 | 7.8 | 18.3 | 28.7 | 24.8 | 27.2 | 24.3 |
| | | 4.6 | 5.2 | 6.1 | 12.9 | 12.3 | 11.1 | 8.7 |
| | With Treatment | 18.0 | 20.0 | 33.8 | 41.0 | 44.1 | 44.4 | 46.6 |
| | | 6.8 | 5.7 | 13.9 | 13.6 | 11.6 | 10.2 | 9.1 |
| | ttest | 0.0006 | 0.0008 | 0.0262 | 0.0895 | 0.0064 | 0.0063 | 0.0003 |

Values are listed as mean ± SD
n = 9 without treatment
n = 7 with treatment

TABLE 4

FECAL OUTPUT

| | | Post Op Day 1 | Post Op Day 2 | Post Op Day 3 | Post Op Day 4 | Post Op Day 5 | Post Op Day 6 | Post Op Day 7 |
|---|---|---|---|---|---|---|---|---|
| Fecal Output (grams) | Without Treatment | 0.4 | 1.5 | 3.0 | 5.1 | 4.6 | 4.6 | 5.4 |
| | | 0.4 | 1.0 | 1.7 | 3.1 | 2.7 | 2.4 | 2.1 |
| | With Treatment | 4.1 | 4.9 | 7.9 | 10.8 | 11.2 | 12.2 | 12.3 |
| | | 2.9 | 3.0 | 3.5 | 4.0 | 3.7 | 3.5 | 3.1 |
| | ttest | 0.0154 | 0.0244 | 0.0088 | 0.0089 | 0.0025 | 0.0005 | 0.0005 |

Values are listed as mean ± SD
n = 9 without treatment
n = 7 with treatment

Further results were obtained by continued experimentation, including (a) a summary of measurements of organ adhesion in the peritonitis model and using the cocktail as treatment; and (b) the results on organ adhesion (with a mechanical abrasion on the surface of the intestine to simulate the gloves of a surgeon) with an image of a typical ileus that develops in this model. The treated intestines look like a completely normal intestine.

Figure 2:
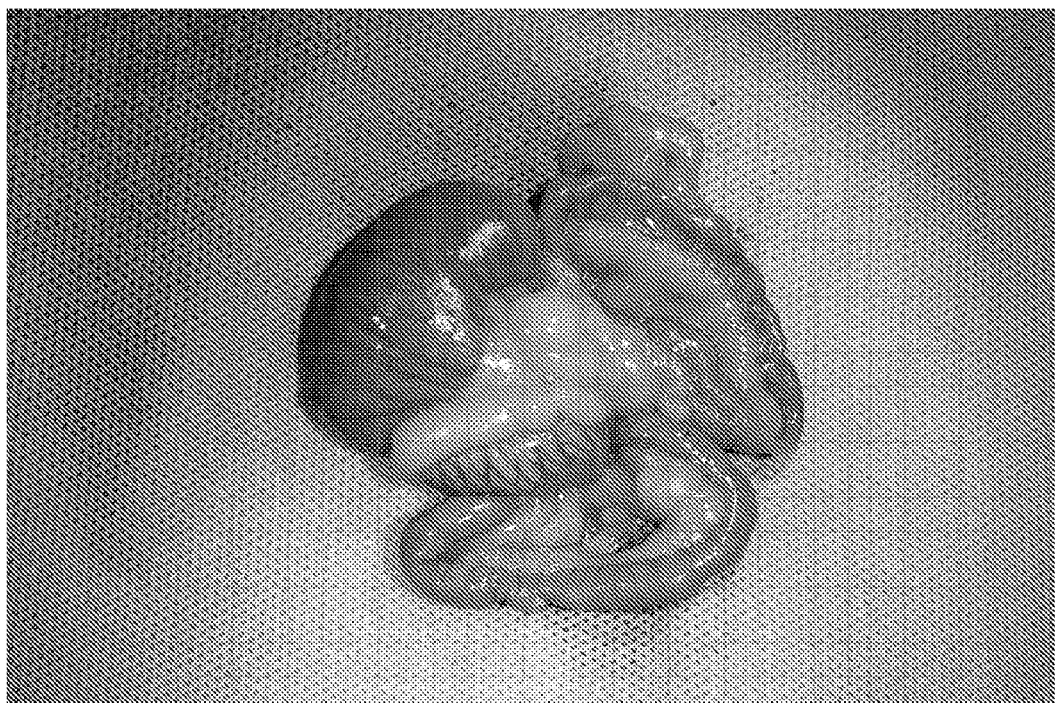
FIG. 2 shows an example view of an intestine treated for adhesion.

In the organ adhesion study with peritonitis model, abdominal organ adhesion after acute peritonitis (by administration of 300 mg/kg cecal material into the peritoneal space) was determined after a period of approximately two months. In control rats without protease inhibition in the lumen of the intestine the frequency of organ adhesion among abdominal organs was 100%. (See FIG. 1.) The frequency of organ adhesion in the treated group was close to zero. (See FIG. 2.)

Figure 3:
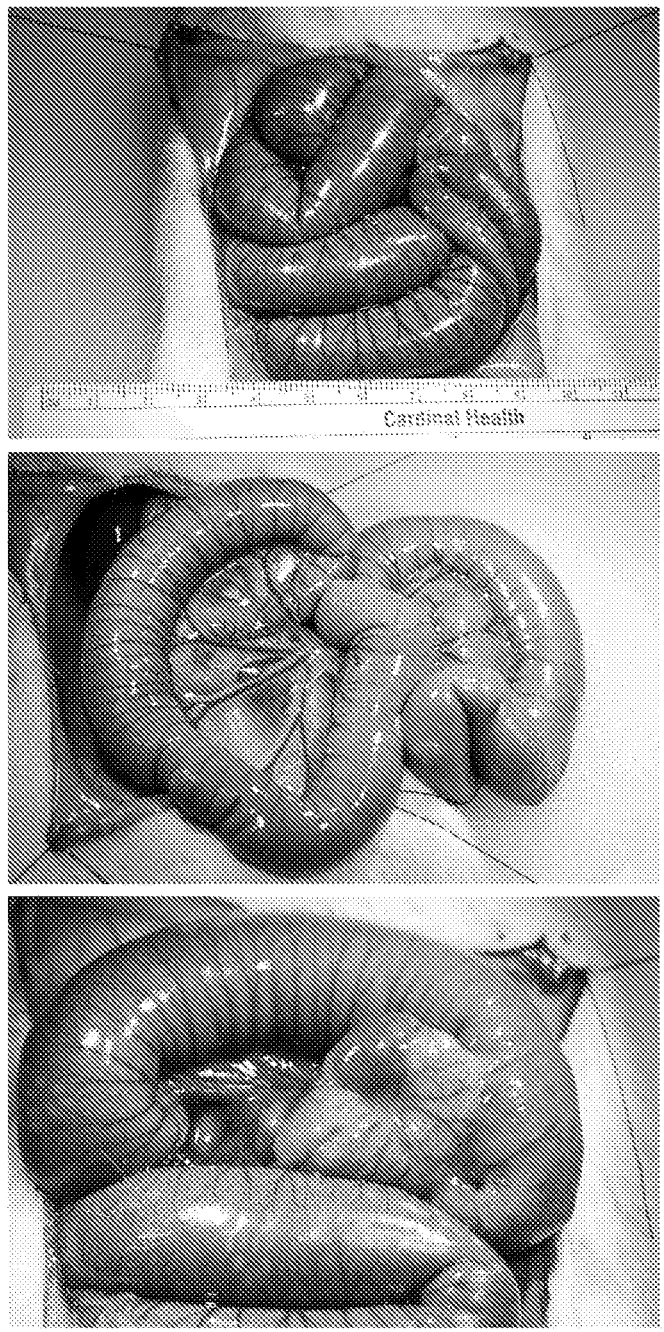
FIG. 3 shows an example view surgical protocol to determine the efficacy of the present treatment.

An example of organ adhesion after mechanical abrasion of the mesothelial cell surface layer with development of distended small intestine after a period two months. The surface of the intestine and cecum were mechanically damaged over a length of about 7 cm and developed an ileum with distended intestine at sites that are located upstream of the abrasion site. (See FIG. 3.) The actual adhesion site is not shown in the image since it is located below the intestine that is shown. Such an ileus was seen in 100% (8/8) untreated animals. Such development of adhesion with ileus was not observed in the treated animals (0/8).

Another study was conducted to determine whether the pancreatic digestive enzymes blockade in the peritoneum reduces postsurgical organ adhesion. The study indicated a number of findings: Treated animals recover from surgery/anesthesia (same dose) quicker than non-treated animals and do not lose as much weight after surgery when compared with non-treated animals. Treated animals return to initial weight after surgery faster than non-treated animals (7 day observation period).

Further, treated animals consume more food and water, and produce greater numbers of fecal pellets (both number and weight) than non-treated animals (7 day observation period). In terms of adhesion, the following were observed using this treatment: no adhesions of abdominal fat to mechanical trauma site was observed in treated animals; no adhesions of mechanical trauma site to abdominal wall in treated animals; no saponification nodes observed in treated animals. The force required to separate adhesion site in treated animals was less in treated animals when compared to non-treated animals. In three animals, the force required to separate adhesion site ranged from 40-70 grams whereas in non-treated animals the force required to separate adhesion site exceeded the limits of the force transducer (100 grams). The adhesion site in non-treated animals induced a narrowing of the intestine which in turn caused an obstruction of intestine. There was a heavy fibrous layer around the adhesion site. The adhesion site in non-treated animals caused the cecum and small intestine proximal to the cecum to form a ball-shaped appearance. Mechanical trauma was produced by 50 grams 40 wipes, cotton swab covered by surgical glove. Animals used were mature Wistar male rats, 350-400 grams. Observation period was 30-35 days. Anesthesia used was Sodium Nembutal, 50 mg/kg, I.P. Treatment was Cyklokapron loading of lumen in small intestine and cecum and a mixture of Cyklokapron and Ciprofloxacin in abdominal cavity.

Finally, a study was conducted to determine whether an enteral and peritoneal blockade of serine proteolytic enzymes accelerates post-surgical bowel function recovery. Mechanisms for post-surgical intestinal dysfunction resulting in a post operative ileus (POI) remain undefined. Delay in post-surgical bowel function may be in part due to an impeded repair process secondary to an accumulation and activity of serine proteolytic enzymes during alimentary tract surgery which occurs in both the intestinal lumen and peritoneal cavity. Enteral and peritoneal lavage with a serine protease inhibitor may improve recovery.

This experiment was conducted by following the procedure: one centimeter ileal resection six centimeters from the ileo-cecal valve and primary anastomosis was created in nine [five non-treated (Non-TR) and four treated (TR)] adult male Wistar rats. Animals were treated with a serine protease inhibitor via an intestinal intra-lumen (tranexamic acid in polyethylene glycol), and peritoneal (tranexamic acid, ciprofloxacin in saline) lavage and allowed to recover. Return time to oral intake, amount of water and food ingestion, and urine output were monitored daily. Results were expressed in mean±standard deviation. A t-test with significance $p<0.05$ was used to compare groups.

The results indicated that treated animals returned to an earlier oral intake [POD 1 (TR) versus POD 2 (Non-TR)], and had an accumulated (POD 7) increase in water consumption [34.4±13.8 gm (TR) versus 22.1±13.3 gm (Non-TR)], food consumption [17.0±8.8 gm (TR) versus 10.6±7.2 gm (Non-TR)] and urine output [49.6±21.2 gm (TR) versus 33.6±20.4 gm (Non-TR)].

These results suggest that serine proteases in the intestinal lumen and peritoneal fluid may prolong POI and that blockade of these enzymes may accelerate alimentary tract recovery following abdominal surgery.

The foregoing disclosure of the preferred embodiments of the present subject disclosure has been presented for purposes of illustration and description. It is not intended to be exhaustive or to limit the subject disclosure to the precise forms disclosed. Many variations and modifications of the embodiments described herein will be apparent to one of ordinary skill in the art in light of the above disclosure. The scope of the subject disclosure is to be defined only by the claims appended hereto, and by their equivalents.

Further, in describing representative embodiments of the present subject disclosure, the specification may have presented the method and/or process of the present subject disclosure as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present subject disclosure should not be limited to the performance of their steps in the order written, and one skilled in the art can readily appreciate that the sequences may be varied and still remain within the spirit and scope of the present subject disclosure.

What is claimed is:

1. A method for treating ileus, the method comprising:
   administering into the lumen of an intestine of an individual a first therapeutic dose comprising a protease inhibitor; and
   administering to an abdominal cavity of the individual a second therapeutic dose comprising a combination of the same protease inhibitor used in the first therapeutic dose and an antibacterial compound.

2. The method of claim 1, wherein the protease inhibitor is effective for inhibiting the function of one or more of the following: serine protease, plasma protease, MMP, amylase and lipase.

3. The method of claim 2, wherein the protease inhibitor is cyclokapron.

4. The method of claim 3, wherein the dose of cyclokapron is 10 to 50 mg/100 ml.

5. The method of claim 1, wherein the antibacterial compound is effective against gram-positive and gram-negative bacteria.

6. The method of claim 5, wherein the antibacterial compound includes one or more of ciprofloxacin, metronidazole, imipenem and cilastatin, ticarcillin and clavulanate, cefuroxime, doxycycline.

7. The method of claim 1, wherein the first and second therapeutic doses are administered prophylactically.

8. The method of claim 1, wherein the second therapeutic dose further comprises an inflammatory lipid mediator binding protein.

9. The method of claim 8, wherein the inflammatory lipid mediator binding protein is albumin.

10. The method of claim 9, wherein the dose of inflammatory lipid mediator binding protein is 10 to 50 mg/100 ml.

11. A method for treating abdominal dysfunction, the method comprising:
   administering into the lumen of an intestine of an individual a first therapeutic dose comprising a protease inhibitor; and
   administering to an abdominal cavity of the individual a second therapeutic dose comprising a combination of the same protease inhibitor used in the first therapeutic dose and an antibacterial compound.

12. The method of claim 11, wherein the protease inhibitor is effective for inhibiting the function of one or more of the following: serine protease, plasma protease, MMP, amylase and lipase.

13. The method of claim 12, wherein the protease inhibitor is cyclokapron.

14. The method of claim 13, wherein the dose of cyclokapron is 10 to 50 mg/100 ml.

15. The method of claim 11, wherein the antibacterial compound is effective against gram-positive and gram-negative bacteria.

16. The method of claim 15, wherein the antibacterial compound includes one or more of ciprofloxacin, metronidazole, imipenem and cilastatin, ticarcillin and clavulanate, cefuroxime, doxycycline.

17. The method of claim 11, wherein the first and second therapeutic doses are administered prophylactically.

18. The method of claim 11, wherein the second therapeutic dose further comprises an inflammatory lipid mediator binding protein.

19. The method of claim 18, wherein the inflammatory lipid mediator binding protein is albumin.

20. The method of claim 19, wherein the dose of inflammatory lipid mediator binding protein is 10 to 50 mg/100 ml.

* * * * *